United States Patent [19]

Tucci et al.

[11] Patent Number: 4,937,557
[45] Date of Patent: Jun. 26, 1990

[54] MONITORING AND INDICATING CIRCUIT FOR REVERSE OSMOSIS FILTER

[75] Inventors: Mario A. Tucci, St. Paul; George K. Sutherland, White Bear Lake, both of Minn.

[73] Assignee: Aqua-Tronics, Inc., St. Paul, Minn.

[21] Appl. No.: 460,014

[22] Filed: Jan. 2, 1990

[51] Int. Cl.$^5$ ............................................. G08B 21/00
[52] U.S. Cl. ..................................... 340/603; 340/607; 210/96.2; 210/85
[58] Field of Search ............... 340/607, 603; 210/96.2, 210/85, 104, 141, 746, 739

[56] References Cited

U.S. PATENT DOCUMENTS

| | | | |
|---|---|---|---|
| 3,841,483 | 10/1974 | Overton | 210/87 |
| 3,990,066 | 11/1976 | Malmgren | 340/603 |
| 4,498,982 | 2/1985 | Skinner | 210/96.2 |
| 4,587,518 | 5/1986 | King | 340/603 |
| 4,623,451 | 11/1986 | Oliver | 210/96.2 |
| 4,708,791 | 11/1987 | Dillard | 210/92.2 |
| 4,744,895 | 5/1988 | Gales et al. | 210/96.2 |
| 4,762,611 | 8/1988 | Schipper | 210/85 |
| 4,784,763 | 11/1988 | Hambleton et al. | 210/90 |
| 4,806,912 | 2/1989 | Clack | 340/603 |
| 4,849,098 | 7/1989 | Wilcock et al. | 210/85 |

Primary Examiner—Joseph A. Orsino
Assistant Examiner—Kinfe-Michael Negash
Attorney, Agent, or Firm—Haugen and Nikolai

[57] ABSTRACT

A monitor and indicating circuit for use with a reverse osmosis filter for signaling the need for servicing of the filter comprises first and second conductivity cells respectively located in the water inlet and outlet pipes of the filter. An AC signal of a predetermined frequency and amplitude is used to drive an op amp whose input resistance comprises the outlet conductivity cell and whose feedback impedance comprises the inlet conductivity cell. Normally, the resistivity of the outlet conductivity cell is substantially larger than the resistivity of the inlet conductivity cell, assuming that the filter is functioning properly. As the ROF fails, the resistivity at the outlet approaches that at the inlet thereby increasing the gain of the variable gain amplifier. The output from the variable gain amplifier is then peak detected and applied to a comparator where it is compared to a predetermined reference voltage. If the output from the peak detector remains below the comparator's reference, the logic means operates to cause a green LED to be illuminated. However, as the filter becomes used, the gain of the operational amplifier approaches unity and the comparator will produce a signal causing a red LED to be lit.

8 Claims, 2 Drawing Sheets

MONITORING AND INDICATING CIRCUIT FOR REVERSE OSMOSIS FILTER

BACKGROUND OF THE INVENTION

1. Field of The Invention:

This invention relates generally to circuitry for monitoring the state of contamination of a reverse osmosis filter used to purify drinking water, and more particularly to a circuit for comparing the concentration of total dissolved solids at the inlet and outlet of such a filter and for providing an indication that the filter is in need of service when the difference drops below a predetermined level.

2. Discussion of the Prior Art:

So-called reverse osmosis water purification systems are finding increased commercial and residential use. Water supplied by many municipalities contain a variety of dissolved (ionized) solids that can affect the flavor and potability of the water.

A typical reverse osmosis filtering system incorporates a cartridge housing containing a semi-permeable membrane and placed in a water supply line downstream of any water softening equipment that may be present. The membrane in question exhibits a propensity for equalizing the concentration of metallic ions dissolved in the water on opposed sides of the membrane. If the concentration of ions in the water is greater on one side than on the other, the water will pass through from the side of lesser ion concentration to the side of greater ion concentration. The force causing the water to move is, of course, the osmotic pressure. By increasing the pressure on the fluid on the side of the membrane exhibiting the greater metallic ion concentration, the flow of water due to osmotic pressure can be reversed. At this point, the membrane functions as a filter for separating the metallic ions from the water in which they are dissolved.

With time, the membrane becomes contaminated in that its pores become plugged with contaminants and the ability of the membrane to separate out dissolved solids drops and replacement of the filter cartridge is required.

It is, of course, advantageous to provide a means for signaling the homeowner or commercial customer that the RO cartridge is in need of replacement. Mere passage of time cannot be relied upon as a good indicator since the condition of the filter membrane can change abruptly, for example, when the municipality may change wells or incorporate an additive into the water supply for one purpose or another.

The Malgren U.S. Pat. No. 3,990,066 describes a RO filter system in which conductivity sensors are disposed on the inlet and outlet sides of the filter cartridge and a Whetstone bridge network is used to detect a change in conductivity of the water flowing at the outlet of the RO filter as compared to that at its inlet. When the bridge reaches a predetermined state of unbalance, a signal is given. Indicator circuits of the type described in the Malgren patent are somewhat unreliable, especially when it is considered that temperature changes of the water affect the conductivity thereof. False alarms tend to be frequent.

The Gales et al U.S. Pat. No. 4,744,895 also discloses an indicator circuit for use with a RO filter and is operative to cause a green or a red LED to be lit, depending upon whether the water is of sufficient purity or not, respectively. The system of that patent employs a single conductivity cell which forms a voltage divider with a variable resistor whose value can be set to correspond to an acceptable water conductivity level. The centerpoint of the voltage divider is then connected through a bistable inverting amplifier exhibiting hysteresis which, in turn, drives the LEDs. Again, taking into account the manner in which water conductivity changes with temperature, the Gales circuit also suffers from erratic control occasioned by temperature swings in the water supply and, further, is not easily tailored to accommodate conductivity changes occasioned by changes made by the municipality as, for example, when changing wells.

OBJECTS

It is accordingly a principal object of the present invention to provide an improved monitoring and indicating circuit for a reverse osmosis water filtering system.

Another object of the invention is to provide a monitoring and indicating circuit for a reverse osmosis water filtering system which is more reliable in its operation than known prior art devices designed for the same purpose.

Yet another object of the invention is to provide a monitoring and indicating circuit for use with a reverse osmosis water filter system which is unaffected by temperature swings in the water supply.

A further object of the invention is to provide a monitoring and indicating circuit for a reverse osmosis filtering system which is low in cost, readily installed, simple to maintain, and reliable in operation.

SUMMARY OF THE INVENTION

In accordance with the present invention, a pair of conductivity cells are employed, one being disposed in the inlet pipe upstream of the ROF and the other in the outlet pipe on the downstream side. When the ROF is effectively operating, a substantial difference in conductivity is measured by the two cells. When the ROF becomes contaminated through use and ceases to properly filter, the conductivity measured by the downstream cell will reflect an increase toward the value being measured by the upstream cell. When the downstream conductivity value becomes more than a preselected percentage of the upstream value, a visual indication is given to reflect the need for servicing of the ROF.

To achieve the foregoing desired result without false indications being given for reasons other than the filter's contamination, the downstream conductivity cell is configured to be the input resistance to an operational amplifier while the upstream cell is wired in as a feedback element for that operational amplifier. The gain of any operational amplifier is proportional to the ratio of its feedback resistance to its input resistance. As such, by comparing the peak DC voltage at the output of the operational amplifier with the peak voltage corresponding to the input AC driving signal, a logic level is created whose state is indicative of whether the removal of the dissolved solids by the ROF is higher than a preset level or, alternatively, below that level. The logic signal is then used to control the on/off state of a pair of LEDs, one red and one green. Because water temperature affects both cells equally, the gain ratio of the op amp remains constant and false signalling is obviated.

The system of the present invention remains relatively insensitive to changes in water temperature by placing the upstream and downstream conductivity cells as close to the filter cartridge as practical. By doing so, there will be a minimum volume of water between the electrodes and they will tend to be at the same temperature. Moreover, the resistivity of the inlet and outlet water can change drastically, but because it is the change in the ratio of these two resistivities that is of importance, such resistivity changes due to changes in the municipal water supply will not cause false triggering.

DESCRIPTION OF THE DRAWINGS

The foregoing features, objects and advantages of the invention will become apparent to those skilled in the art from the following detailed description of the preferred embodiment, especially when considered in conjunction with the accompanying drawings in which like numerals in the several views refer to corresponding parts.

DESCRIPTION OF THE PREFERRED EMBODIMENT

Figure 1:
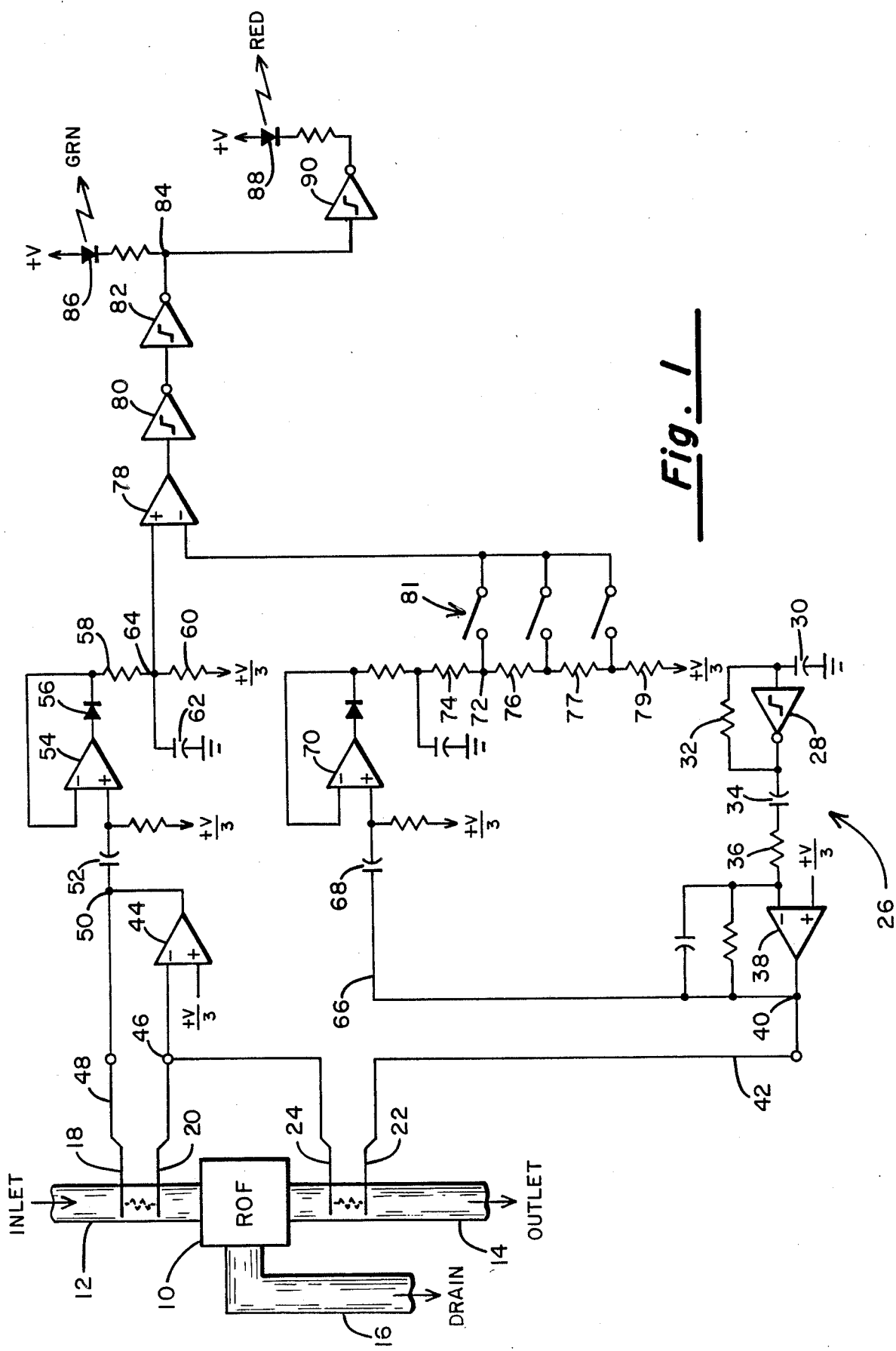
FIG. 1 is an electrical schematic diagram of the reverse osmosis filter monitor and indicating circuit in accordance with a first embodiment.

Referring to FIG. 1, there is shown a reverse osmosis filter 10 disposed between a water inlet pipe 12 and a water outlet pipe 14. The water flowing in the inlet pipe is, of course, unfiltered while that flowing in the outlet pipe 14 is filtered, provided the ROF 10 is in operating condition and effective. The portion of the flow applied to the ROF but incapable of passing through the filter because of its flow constraints exits the system through a drain connection 16.

The inlet pipe 12 and outlet pipe 14 are preferably formed from PVC and, as such, exhibit high electrical resistance. Inserted through the wall of the inlet pipe 12 as close to the ROF 10 as is physically practical are a pair of closely spaced stainless steel electrodes 18 and 20 which together, serve as a conductivity oell for the untreated water. In a like fashion, a pair of stainless steel electrodes 22 and 24 pass through the wall of the plastic outlet pipe 14 and are spaced apart from one another identically to the spacing between electrodes 18 and 20 comprising the inlet pipe.

The circuit of the present invention includes a drive oscillator, indicated generally by numeral 26, which is seen to include a Schmidt trigger invertor circuit 28 having a capacitor 30 connected between its input terminal and ground and a feedback resistor 32 connected in parallel with the invertor 28. The component values for the capacitor 30 and the resistor 32 may be selected so as to produce a 1 KHz AC signal. This signal is coupled through a series connection of a capacitor 34 and a resistor 36 to the inverting input of an operational amplifier 38 which serves to attenuate the voltage to a reference level. That is, the non-inverting input is coupled to a source of reference potential and appearing at the output junction 40 is a conditioned and attenuated 1 KHz, 1.5 volt peak-to-peak signal exhibiting a low impedance source characteristic for driving the circuitry yet to be described, as well as the conductivity cells comprising electrodes 18-20 and 22-24 in the inlet and outlet pipes, respectively More specifically, the conditioned AC signal at junction 40 is applied, via a conductor 42, to the electrode 22 of the conductivity cell in the output pipe 14. The electrode 24 of that conductivity cell is connected to the inverting input or summing junction of a further op amp 44. Hence, the resistance between electrodes 22 and 24 in the outlet water stream of the ROF 10 becomes the input resistance of the inverting op amp 44. Electrode 20 of the conductivity cell in the inlet pipe 12 is also connected to the summing junction 46 of the op amp 44 while the other electrode 18 of the inlet side conductivity cell is connected by a conductor 48 to the output junction 50 of the op amp 44. Thus, the resistance between electrodes 18 and 20 becomes the feedback element for the op amp. As those skilled in the art appreciate, the gain of the inverting op amp 44 is proportional to the ratio of the feedback resistance to the input resistance. Op amp 44 thus comprises an inverting amplifier stage where the gain is proportional to the ratio of the resistivity of the unfiltered inlet water to the resistivity of the filtered outlet water.

Typically, the filtered outlet water will have a lower quantity of total dissolved solids (TDS) than the unfiltered inlet water so that the op amp 44 normally has a gain less than one. The 1.5 volt peak-to-peak signal supplied by the conditioning amplifier 38, via conductor 42, is thus attenuated by the rejection of the dissolved solids by the ROF 10. The signal appearing at the output junction 50 can thus be considered as an attenuation of the water condition indicating signal at junction 40, the attenuation being a measure of the percentage of rejection of TDS of the ROF 10.

The output from the operational amplifier 44 appearing at junction 50 is coupled through a capacitor 52 to the non-inverting input of an operational amplifier 54 configured as a peak detector by virtue of the diode 56 coupled between the output of op amp 54 and its inverting input. A voltage divider, including precision resistors 58 and 60, along with a holding capacitor 62 coupled between ground and the common junction 64 between the precision resistors 58 and 60, results in the voltage at junction 64 corresponding to the peak voltage measured at junction 50.

The 1.5 volt 1 KHz conditioned signal at junction 40 is applied over a conductor 66 and a coupling capacitor 68 to the non-inverting input of an operational amplifier 70 also configured as a precision peak detector identical to that comprising the operational amplifier 54. The voltage signal developed at junction 72 thus corresponds to the peak input voltage appearing at junction 40. The resistance values of series connected resistors 74, 76, 77 and 79 are selected using switches indicated generally by numeral 81 so that the output from the peak detector 70 will be attenuated by the same percentage.

A comparator stage, including operational amplifier 78, receives as its inputs the peak voltages developed at junctions 64 and 72 and thus compares the two attenuated AC signals, providing a logic level that will be a binary low when the percentage of rejection of TDS by the ROF is higher than that required by the setting of the voltage divider comprising resistors 74, 76, 77 and 70 by switches 81. The output from op amp 78 will be high when the percentage of rejection of the filter is less than the required setting. A pair of invertors 80 and 82 are connected in series between the output of comparator 78 and a junction 84. The green LED diode 86 is connected between a source of DC potential (+V) and the junction 84, Likewise, the red LED 88 is connected between the same voltage source and the junction 84, via an invertor 90. Thus, When the percentage rejection provided by the ROF is higher than a preset threshold voltage developed at the junction 72, the green LED 86 will be illuminated. However, when the percentage rejection drops below the threshold, the output from the comparator 78 will shift causing the red LED 88 to glow.

The reverse osmosis filter monitor and indicating circuit shown in FIG. 1 is relatively insensitive to changes in water temperature because the electrodes 20 and 24 (inlet and outlet) are physically placed as close as possible to the reverse osmosis filter cartridge 10. As a result, a minimum volume of water exists between the upstream and downstream electrodes and because of the close spacing between the two, their temperature will tend to be the same.

As mentioned earlier, if the reverse osmosis filter is working properly, the changing of the water source by a municipality switching wells will not affect circuit performance adversely because the water at the outlet of the reverse osmosis filter 10 will still have a resistivity that is a percentage of that of the inlet water. Hence, even if drastic changes occur in the resistivity of the inlet and outlet water, the circuit of the present invention will not yield a false indication since the ratio of the two resistivities will tend to remain constant.

ALTERNATIVE EMBODIMENT -- FIG. 2

Figure 2:
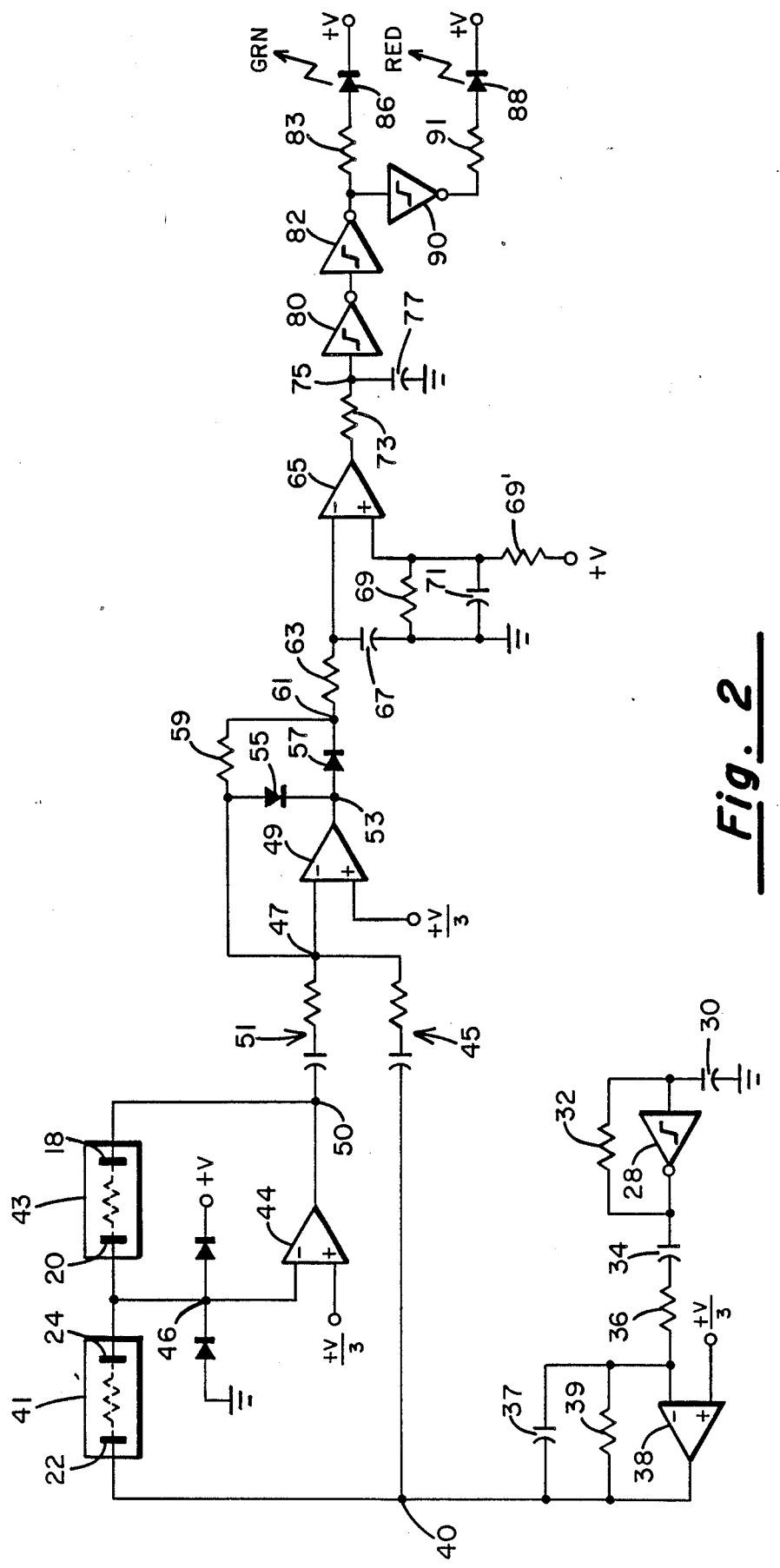
FIG. 2 is an electrical schematic diagram of the reverse osmosis filter monitor and indicating circuit in accordance with an alternative embodiment.

The embodiment of FIG. 2 also includes a free running oscillator comprising a Schmidt trigger invertor 28 having an input capacitor 30 connected between ground and its input and a feedback resistor 32 connected in parallel with the Schmidt trigger invertor 28. The components are selected such that a 1 KHz AC waveform is produced. However, since the circuit will operate over a fairly wide range of frequencies, limitation to the 1 KHz frequency should not be inferred. As in the embodiment of FIG. 1, the 1 KHz signal is applied, via a coupling capacitor 34 and an input resistor 36, to the inverting input of a signal conditioning circuit including an op amp 38 and a parallel combination of a capacitor 37 and a resistor 39. A 1.5 volt peak-to-peak signal is developed at the junction point 40.

The filter outlet conductivity cell, which includes electrodes 22 and 24, is enclosed by box 41 while the conductivity cell associated with the inlet side of the ROF including electrodes 18 and 20 is identified as being enclosed by the box 43. As in the embodiment of FIG. 1, the electrode 20 of the conductivity cell 43 on the inlet side of the ROF is connected to the inverting input or summing junction of an op amp 44 while the other electrode 18 thereof is connected to the output junction 50 of that op amp. As such, the conductivity cell 43 again comprises a feedback resistance corresponding to the resistivity of the unfiltered inlet water between electrodes 18 and 20.

The 1.5 volt peak-to-peak, 1 KHz signal at junction 40 is applied to the electrode 22 of the conductivity cell 41 in the outlet of the ROF and its other electrode 24 is also tied to the summing junction of the op amp 44. The diodes connected between ground and junction 46 and junction 46 to the DC voltage, +V, serve to suppress transients which might be impressed. The resistance of the water between the electrodes in the outlet conductivity cell 41 comprises an input resistance for the inverting op amp 44. In accordance with the alternative embodiment now being described, the signal applied to the input resistance of the op amp 44, i.e., the signal at junction 40 is applied through a capacitor-resistor series network 45 to a current summing node 47 while the output from the op amp 44 is coupled through an identical series resistance-capacitance network 51 to that same summing point 47. In that op amp 44 is designed to operate in the inverting mode, meaning that its output is opposite in phase from its input, the signal passing through the peak sensing op amp 49 will comprise the algebraic sum of the two currents through the networks 45 and 51. The capacitance circuits 45 and 51 decouple the DC supply and filter low frequency noise signals such as 60 Hz noise. The two currents at junction 47 are proportional to the input voltage at junction 40 and the output voltage at junction 50 of the op amp 44. Looking at it slightly differently, this is the same as saying that the two currents being algebraically summed are proportional to the resistance of the conductivity cells 41 and 43, with the signal at junction 47 being a quantitative representation of the percentage of the rejection of total dissolved solids by the ROF. Op amp 49 along with the diode 57 and the resistor 59 comprises a voltage peak sensing circuit. The diode 55 functions to hold the operational amplifier 49 in its linear region.

The signal appearing at junction 61 can be used directly to drive an analog volt meter or any other kind of indicator for signaling the condition of the ROF, but where it is desired to signal a properly working filter with a green indicator and a filter needing attention with a red indicator, the circuitry to the right of junction 61 in FIG. 2 may be used. The peak pulsating signal appearing at junction 61 is converted to a DC level by the series resistor 63 and the shunt capacitor 67 connected to ground. This DC signal is applied to the inverting input of an op amp 65 configured as a comparator where the signal applied to the inverting input is compared to a predetermined reference established by the resistive voltage divider comprising resistors 69 and 69' tied between the DC supply terminal and ground.

The output from the comparator is coupled through the resistance 73 to a junction point 75. A capacitor 77 is connected between that junction and ground. Serially connected Schmidt trigger invertors 80 and 82 and a current limiting resistor 83 are disposed in series with the cathode of the green LED 86. Its anode electrode is tied to the DC supply. The red LED 88 is coupled to the output of Schmidt trigger invertor 82 by a further Schmidt trigger invertor 90 and a current limiting resistor 91. When the power is first applied to the circuit of FIG. 2 by closing a push button "filter test" switch (not shown), and before the comparator 65 provides its output indicative of the condition of the ROF, the capacitor 77 insures that the green LED 86 will first be illuminated. Subsequently, the green light will remain illuminated if the comparator output remains low However, if the DC signal applied to the inverting input of the comparator 65 exceeds the reference voltage such that the output of comparator 65 goes high, then the green LED 86 will be extinguished and the red LED will be illuminated.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. A monitoring and indicating circuit for a reverse osmosis water filtering system of the type having a raw water inlet pipe and a filtered water outlet pipe and a reverse osmosis filter cartridge disposed therebetween, comprising:
   (a) first and second conductivity cells, the first disposed in said water inlet pipe and the second in said water outlet pipe;
   (b) variable gain amplifier means including an operational amplifier having an input terminal and an output terminal;
   (c) signal generating means for producing an AC signal of a predetermined frequency and amplitude;
   (d) means coupling said second conductivity cell in series between said signal generating means and said input terminal of said operational amplifier;
   (e) means coupling said first conductivity cell between said output terminal and said input terminal of said operational amplifier;
   (f) peak detecting means with an input terminal connected to said output terminal of said operational amplifier and an output terminal;
   (g) comparator means for comparing a signal proportional to the peak-voltage signal at said output terminal of said peak detecting means with a predetermined reference voltage; and
   (h) indicator means coupled to said comparator means for indicating whether said signal proportional to the peak voltage signal is greater than or less than said predetermined reference voltage.

2. The monitoring and indicating circuit as in claim 1 wherein said first and second conductivity cells each include a pair of electrodes disposed in longitudinally-spaced relation in said water inlet pipe and said water outlet pipe, respectively, with the spacing between the electrodes in each pair being equal and said electrodes being electrically insulated from one another when no liquid is present in said inlet and outlet pipes.

3. The monitoring and indicating circuit as in claim 1 wherein said predetermined reference voltage is proportional to the peak value of said AC signal from said signal generating means.

4. The monitoring and indicating circuit as in claim 1 wherein said predetermined reference voltage is a fixed direct current voltage value.

5. The monitoring and indicating circuit as in claim 1 and further including circuit means for algebraically summing a current signal from said operational amplifier output terminal with a current signal from said signal generating means, said further circuit means being coupled to said input terminal of said peak detecting means.

6. The monitoring and indicating circuit as in any one of claims 1 through 5 wherein said indicator means comprises at least one LED coupled to the output of said comparator means.

7. The monitoring and indicating circuit as in any one of claims 1 through 5 wherein said indicator means comprises a pair of LEDs, and logic means coupling said pair of LEDs to the output of said comparator means for illuminating only one of said pair of LEDs at a time, the one illuminated being determined by the output of said comparator means.

8. The monitoring and indicating circuit as in claim 2 wherein one of said pair of electrodes in said outlet pipe is connected to said signal generating means, the other of said pair of electrodes in said outlet pipe is connected in common with one of said electrodes in said inlet pipe and to said input terminal of said operational amplifier and the other of said electrodes in said inlet pipe is connected to said output terminal of said operational amplifier.

* * * * *